USOO5653740A

United States Patent [19]
Degroot et al.

[11] Patent Number: 5,653,740
[45] Date of Patent: Aug. 5, 1997

[54] METHOD AND APPARATUS FOR INDUCTION OF FIBRILLATION

[75] Inventors: Paul J. Degroot, Brooklyn Park; Rahul Mehra, Stillwater, both of Minn.

[73] Assignee: Medtronic, Inc., Minneapolis, Minn.

[21] Appl. No.: 587,309

[22] Filed: Jan. 16, 1996

[51] Int. Cl.$^6$ ........................................ A61N 1/38
[52] U.S. Cl. ............................... 607/72; 607/74
[58] Field of Search ................................... 607/4, 5

[56] References Cited

U.S. PATENT DOCUMENTS

| | | | |
|---|---|---|---|
| 3,602,224 | 8/1971 | Jaros | 607/72 |
| 4,969,463 | 11/1990 | Dahl et al. | 607/5 |
| 5,105,809 | 4/1992 | Bach, Jr. et al. | 607/5 |
| 5,107,834 | 4/1992 | Ideker et al. | 607/5 |
| 5,184,616 | 2/1993 | Weiss | 607/5 |
| 5,215,083 | 6/1993 | Drane et al. | 607/4 |
| 5,279,293 | 1/1994 | Andersen . | |
| 5,346,506 | 9/1994 | Mower et al. | 607/7 |

FOREIGN PATENT DOCUMENTS

| | | | |
|---|---|---|---|
| 0589252 | 3/1994 | European Pat. Off. | 607/5 |

*Primary Examiner*—William E. Kamm
*Assistant Examiner*—George R. Evanisko
*Attorney, Agent, or Firm*—Reed A. Duthler; Harold R. Patton

[57] ABSTRACT

A method and apparatus for inducing fibrillation in a patient, for example to verify the efficacy of a defibrillator system. In the disclosed embodiment, an implantable cardioverter-defibrillator has an output stage coupled via a plurality of leads to the patient's heart. When it is desired to induce fibrillation in the patient, the device's control circuitry initiates an output capacitor charging cycle and subsequent delivery of a multi-phase fibrillation inducing stimulus to the heart. The multiple phases of the stimulus reflect an incremental discharging of the output capacitor. In one embodiment, the stimulus has three phases, with the first two separated by a time interval equal to or slightly less than the patient's "vulnerability window," which is defined as the time period following a paced cardiac event during which repolarization of the cardiac muscle is occurring, rendering the heart susceptible to induced fibrillation. The final phase of the multi-phase waveform reflects an untruncated discharge of the remaining energy on the output capacitor.

15 Claims, 2 Drawing Sheets

METHOD AND APPARATUS FOR INDUCTION OF FIBRILLATION

FIELD OF THE INVENTION

This invention relates generally to the treatment of cardiac arrhythmias, and more particularly relates to a method and apparatus for inducing fibrillation.

BACKGROUND OF THE INVENTION

It has long been recognized that cardiac defibrillation —the termination of an episode of fibrillation—can be accomplished through application of an electrical shock to the cardiac muscle. See, for example, Swartz et al., "Influence of T-Wave Shock Energy on Ventricular Fibrillation Vulnerability in Humans," *Journal of American College of Cardiology*, 1995 Conference Abstracts, February 1995; see also, Karolyi et al., "Timing of the T-Wave Shock for Inducing Ventricular Fibrillation in Patients With Implantable Cardioverter Defibrillators," *PACE NASPE Abstracts*, Vol. 18, April 1995 (Part II), p. 802.

Numerous types of defibrillating devices, both external and implantable, are available for the purpose of cardiac defibrillation through electrical stimulation. One example is the Medtronic Model 7219 Cardioverter-Defibrillator, commercially available from the Assignee of the present invention.

One method of testing a defibrillator's operability to ensure that it is capable of reliably defibrillating the heart involves first inducing an episode of fibrillation in the patient's heart, and then activating the defibrillator to ascertain whether it is capable of terminating the induced fibrillation. A 60-cycle type fibrillator is one device used for inducing fibrillation, although such fibrillators are known to fail to induce fibrillation. Moreover, implantable defibrillator systems are becoming increasingly common, and it is not technically feasible or practical to incorporate a 60-cycle fibrillator into an implantable device.

To address these issues, it has been proposed in the prior art that fibrillation can be induced in either chamber of the heart (atrial or ventricular) by delivering a stimulus during that chamber's repolarization phase, i.e., within a so-called "vulnerability window" following the chamber's depolarization period when the heart has begun to repolarize but has not completely repolarized. This is described, for example, in U.S. Pat. No. 5,129,392 to Bardy et al., entitled "Apparatus for Automatically Inducing Fibrillation," which patent is assigned to assignee of the present invention and hereby incorporated by reference herein in its entirety.

According to the Bardy et al. '392 patent, the pulse intended to induce fibrillation is delivered in a timed relationship with an immediately preceding pacing pulse. An overdrive pacing and capture detection protocol is carried out (or some other method is used) to determine the patient's Q-T interval, enabling a subsequent fibrillation-inducing shock to be delivered at a time known to fall near the end of this interval but prior to the conclusion of the repolarization phase. The Bardy et al. '392 method and apparatus are believed to allow for extremely accurate placement of the fibrillation-inducing shock relative to the refractory period of the patient's heart.

The Medtronic Jewel™ cardioverter/defibrillator is an example of a commercially-available device which is capable of delivering a stimulus during the repolarization phase to induce fibrillation. The Jewel's so-called T-Shock[198] feature requires the programming of three parameters: the rate at which overdrive pacing pulses are delivered (where overdrive pacing refers to pacing at a rate known to be above the patient's natural cardiac rate); the amplitude of fibrillation inducing shocks, and the shock coupling interval, which is the interval from delivery of the last overdrive pacing pulse to the delivery of the fibrillation-inducing shock. Clinical experience has shown that success in inducing fibrillation with the first T-Shock™ pulse occurs roughly 70-to 90% of the time.

Some clinicians may regard programming three parameters to accomplish automatic fibrillation induction as inconvenient or undesirable. Although a set of nominal or default parameters can be specified for the device, such nominal parameters are less likely to be appropriate for some patients, such as those on anti-arrhythmic drugs which slow conduction.

Another way that the success rate for inducing fibrillation might be improved is by increasing the energy content of the fibrillation-inducing shock. For example, a nominal pulse of 0.6J may be increased to 2.0J. However, this may have certain disadvantages, including minor irritation of the myocardium or increased pain for the unsedated patient.

SUMMARY OF THE INVENTION

In view of the foregoing considerations, the present invention is directed to a method and apparatus for inducing episodes of cardiac fibrillation for the purposes of testing the efficacy and reliability of a defibrillator system. In particular, the present invention is directed to a method and apparatus with which the success rate for induction of fibrillation is increased, while at the same time the number of programmable parameters associated with the method and apparatus is decreased.

BRIEF DESCRIPTION OF THE DRAWINGS

The foregoing and other aspects of the present invention may perhaps be best appreciated with reference to a detailed description of a specific embodiment of the invention, when read in conjunction with the accompanying drawings, wherein.

DETAILED DESCRIPTION OF A SPECIFIC EMBODIMENT OF THE INVENTION

Figure 1:
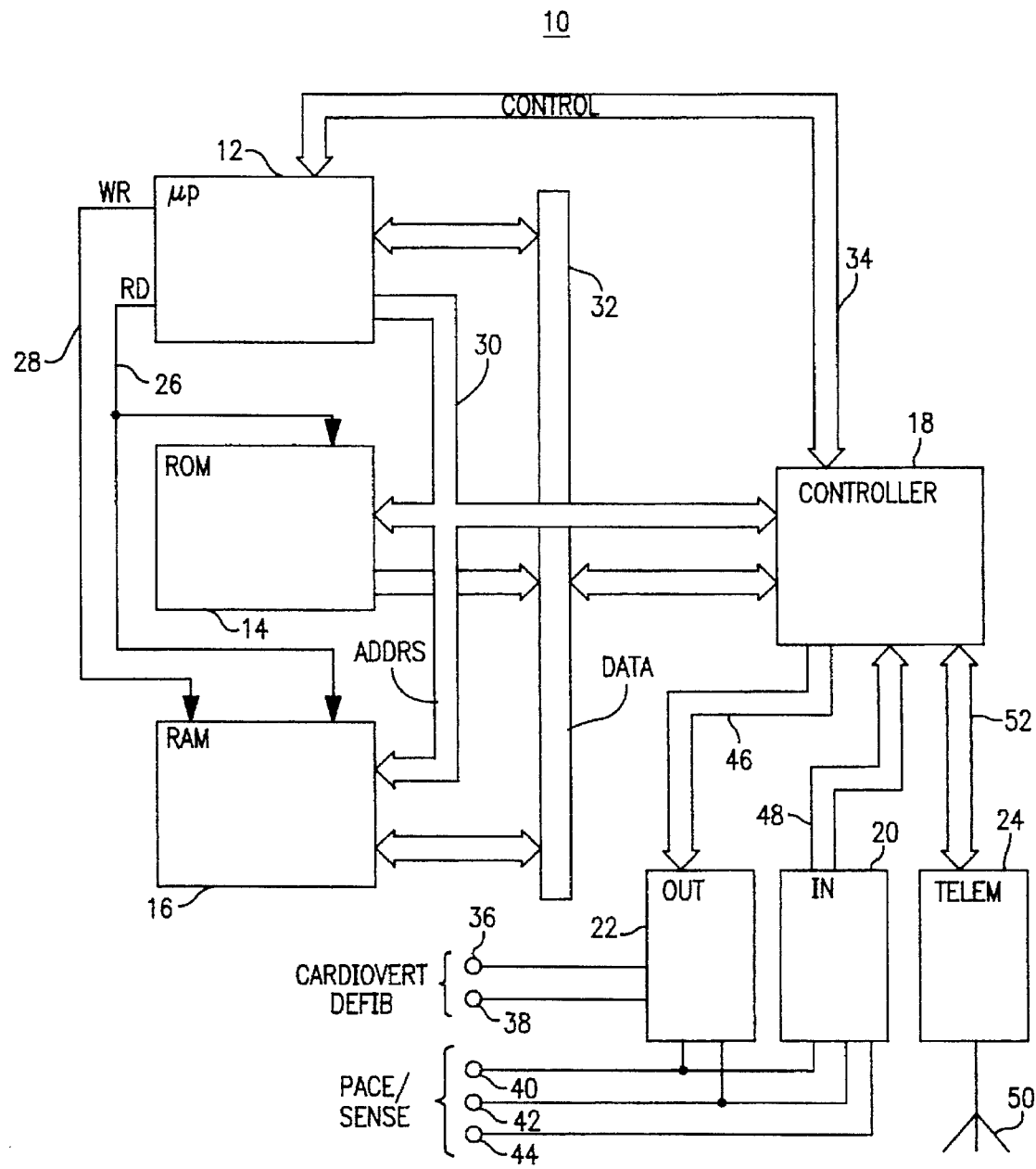
FIG. 1 is a functional block diagram of an implantable cardioversion and defibrillation system with which the present invention may be practiced.

FIG. 1 is a functional block diagram of an implantable cardioverter/defibrillator system 10 of a type with which the present invention may be practiced. Although the invention shall be described herein in connection with the microprocessor-controlled system 10 of FIG. 1, it is believed and is to be understood that the present invention may be advantageously practiced in connection with many different types of systems for the treatment of cardiac disorders, including systems which incorporate a custom integrated circuit controller, or with devices which utilize analog timing and control circuitry. As such, system 10 of FIG. 1 should be considered merely exemplary, rather than limiting, with regard to the scope of applications of the invention.

The primary components of system 10 as shown in FIG. 1 are a microprocessor 12, read-only memory (ROM) 14, random-access memory (RAM) 16, a digital controller circuit 18, input and output amplifiers 20 and 22, respectively, and a telemetry circuit 24. (It is to be understood that the various components of device 10 are powered with an internal power supply, typically a low-voltage, low-current lithium-iodine battery or the like, which for the sake of clarity is not shown in the Figures.)

In accordance with common practice in the art, ROM 14 stores basic programming for the device, including instructions defining the computations to be performed by the device to derive the various timing intervals needed for the device to operate in accordance with a predetermined operational algorithm. RAM 16, on the other hand, may store programming for the device, but also serves to store dynamic values of variable control parameters and the like, such as the programmable pacing rate, programmed cardioversion and defibrillation intervals, pulse widths, pulse amplitudes, and so forth, which are programmed into the device by a physician or clinician. RAM 16 may also store derived values, such as the intervals between detected cardiac events, for example.

The reading of data from ROM 14 and RAM 16 is controlled by an RD line 26. The writing of data to RAM 16 is controlled by a WR line 28. An address bus 30 and a data bus 32 interconnect ROM 14, RAM 16 and microprocessor 12. In response to assertion of the signal on RD line 26 ("the RD signal"), the contents of ROM 14 or RAM 16 designated by the address information present on address bus 30 upon assertion of the RD signal are driven onto data bus 32. Similarly, in response to assertion of a signal on WR line 28 ("the WR signal"), information on data bus 32 is written into a location in RAM 16 designated by the address information then present on address bus 30.

Controller 18 performs the basic timing and control functions for system 10. Controller 18 preferably includes at least one programming timing counter, initiated, for example, upon sensing of ventricular contractions, paced or sensed. This timing counter may be used to define the various timing intervals which must be defined or measured by system 10 in order to operate in accordance with its pacing, cardioverting, and/or defibrillating operational algorithms. The timing intervals which the timing counter in controller 18 counts are controlled by data stored in ROM 14 or RAM 16.

Controller 18 also triggers output pulses from output stage 22, as will be hereinafter described in further detail, and generates interrupts to microprocessor 12 on a control bus. For example, controller 18 may generate interrupts to microprocessor 12 upon the detection of various cardiac events.

Output stage 22 contains a high-energy pulse generator capable of generating cardioverting and/or defibrillating pulses, as will be hereinafter described in further detail. High-energy output pulses from the pulse generator in output stage 22 are applied to the patient's heart (not shown in FIG. 1) via electrodes 36 and 38, which are typically large surface area electrodes disposed on or in the heart. Any of the known prior art cardioversion/defibrillation electrode systems would be suitable for the purposes of practicing the present invention.

Output stage 22 is further coupled to electrodes 40, 42, and 44 which are employed to accomplish bradycardia pacing of the heart. One of electrodes 40, 42, and 44 is typically disposed on the distal end of a cardiac pacing/sensing lead such that it may be situated, for example, at or near the apex of the ventricle of the heart. Another one of electrodes 40, 42, and 44 is preferably a ring electrode spaced back from the distal end of the cardiac pacing/sensing lead. Still another one of electrodes 40, 42, and 44 is typically a common or indifferent electrode, and in one embodiment the implantable device's hermetic, conductive enclosure functions as this indifferent electrode, in accordance with common practice in the art.

Output stage 22 receives control signals from controller 18 via a control bus 46, such that controller 18 can determine the time, amplitude, and pulse width of pulses to be delivered by output stage 22, and to determine which electrodes will be used for delivery of the pulses.

Sensing of heart activity, both intrinsic and stimulated, is accomplished by input amplifier circuit 20, which is also coupled to electrodes 40, 42, and 44. Electrodes 40, 42, and 44 are preferably employed to detect cardiac activity, e.g., ventricular contractions, and may be used to determine whether pacing pulses have captured the heart.

Signals indicating the occurrences of cardiac activity, both paced and sensed, are provided to controller 18 via a bus 48. Controller 18 passes data indicative of the occurrence of various cardiac events to microprocessor 12 via bus 34, in the form of interrupts which serve to prompt microprocessor 12 to perform any necessary calculations and/or update values stored in RAM 16.

External control of implantable system 10 is accomplished via telemetry block 24, which facilitates communication between implantable system 10 and an external programming unit (not shown). Typically, such telemetric communication involves the transmission of radio-frequency signals between implantable system 10 and the external device. Thus, an antenna 50 is typically provided in implantable system 10. Telemetry systems appropriate for the purposes of practicing the present invention are disclosed in U.S. Pat. No. 4,556,063 to Thompson, et al., entitled "Telemetry System for a Medical Device," and in U.S. Pat. No. 5,127,404 to Wyborny et al. entitled "Telemetry Format for Implanted Medical Device." The Thompson et al. '063 and Wyborny et at. '404 patents are each hereby incorporated by reference herein in their respective entireties. An example of a commercially-available external programming unit suitable for the purposes of practicing the present invention is the Medtronic Model 9790 Programmer.

Information received by telemetry circuitry 24 is passed to controller 18 via a bus 52. Similarly, information from system 10 is provided to telemetry block 24 via bus 52 for transmission to the external programming unit.

As noted above, the present invention relates to the inducing of fibrillation in a patient in order to assess the efficacy of a system such as system 10 in FIG. 1 in defibrillating a patient's heart. In accordance with the presently disclosed embodiment of the invention, inducing fibrillation is accomplished through the delivery of a multiple-phase waveform delivered from the discharge of a single energy storage device (e.g., capacitor) in output stage 22.

Figure 2:
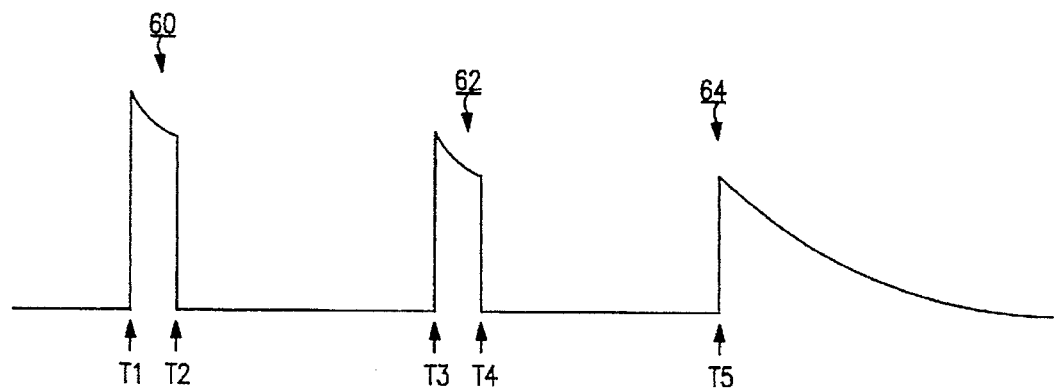
FIG. 2 illustrates a multi-phase waveform of a fibrillation-inducing shock in accordance with one embodiment of the invention.

A multiple-phase fibrillation-inducing waveform in accordance with the presently disclosed embodiment of the invention is illustrated in FIG. 2. The waveform shown in FIG. 2 consists of three pulses or phases 60, 62, and 64, which are initiated at times T1, T3, and T5, respectively. Pulses 60 and 62 are each of predetermined duration, 2-mSec in the presently preferred embodiment. Pulse 64 is, in the embodiment of FIG. 2, untruncated. Pulse 60 has an initial voltage level of V1, which is 100 volts in the presently preferred embodiment. During the 2-mSec duration of pulse 60, the output capacitor from output stage 22 discharges, such that at time T2, the voltage level of pulse 60 has decreased to V2.

As noted above, the vulnerability window for delivery of the a fibrillation pulse is the time interval which begins at some time after the heart depolarization which follows delivery of a pacing pulse and which extends into the repolarization phase that occurs as a result of the stimulated contraction. It is called the vulnerability window since it is during the repolarization phase (but before complete repolarization has occurred) that the heart is susceptible to being stimulated into fibrillation. In one embodiment of the invention, the separation between pulses 60 and 62 of the multi-phase waveform of FIG. 2 (i.e., the time from T2 to T3) is preferably equal to or slightly less than the duration of the vulnerability window for delivery of the first pulse. In this way, the likelihood that either pulse 60 or pulse 62 falls in the vulnerability window is practically ensured, since if pulse 60 is early, i.e., is delivered before the vulnerability window, then pulse 62 will certainly occur within the vulnerability window. Separations wider than the vulnerability window can result in pulses 60 and 62 being delivered before and after the vulnerability window, respectively.

To aid in determining the duration of the vulnerability window, and hence in determining the appropriate separation between pulses 60 and 62, the teachings of the above-identified Bardy et al. '392 patent or the above-identified Karolyi et al. reference can be applied. Such a determination may be made using external equipment in a clinical setting at the time of implant of an implantable defibrillator, or alternatively using circuitry incorporated into the implanted device itself, on a periodic or dynamic basis.

It is contemplated that the separation between pulses 60 and 62 can be specified as a programmable parameter of system 10, with the separation capable of being specified within a range between 50- and 300-mSec, for example. The parameter can be programmed based upon an assessment of a particular patient's normal vulnerability window, or upon statistical data regarding the normal vulnerability window among a large population of patients. As another alternative, the separation between pulses can be fixed, as an unprogrammable operational parameter of device 10, to a value which reflects an average or nominal value among a large population. This latter option has the benefit of reducing the number of parameters which must be programmed, and if a statistically accurate value is chosen, this option would result in a high success rate for induction of fibrillation.

The last pulse 64 in the multi-phase waveform of FIG. 2 is preferably an untruncated discharge of the remaining stimulating pulse energy stored in output stage 22. Experiments have shown that the vulnerability window for long, untruncated pulses is generally wider than for relatively shorter truncated pulses like pulses 60 and 62.

It has been clinically demonstrated that a multi-phase fibrillation pulse such as depicted in FIG. 2 is capable of inducing ventricular fibrillation over a very wide range of coupling intervals, such that the specification of a particular coupling interval is considerably less critical to the efficacy of the pulse in inducing fibrillation. This advantageously allows the use of relatively low pulse energy as compared with the prior art, thereby minimizing current drain on an implantable device's power supply and hence maximizing device longevity.

In addition, since the selection of a coupling interval becomes less critical when practicing the present invention, the need for an overdrive pacing sequence, as proposed in the above-identified Bardy et al. reference, for example, is reduced or eliminated altogether. This similarly has the advantage of minimizing current drain and further leads to simplification of the device's circuitry and operational algorithm.

As noted above, the multi-phase fibrillation inducing waveform of FIG. 2 is generated by output circuit 22. The multi-phase waveform is produced by incrementally discharging an output energy storage device, a capacitor for example, within output circuit 22. As will be appreciated by those of ordinary skill in the art, output capacitors in implantable medical devices are typically charged by a charging circuit which draws its current from the device's power supply.

Numerous types and configurations of charging circuits are well-known in the prior art. It is believed that many such different known types and configurations are suitable for the purposes of practicing the present invention. One example of a charge pump circuit suitable for the purposes of practicing the present invention is described in U.S. Pat. No. 5,265,588 to Nelson et al., entitled "VCO Driven Flyback Converter for Implantable Cardioverter/Defibrillator." The Nelson et al. '588 patent is hereby incorporated by reference herein in its entirety. When controller circuit 18 determines, based upon its operational algorithm, that a fibrillation-inducing pulse is to be delivered, it asserts one or more signals conducted on lines 46 to initiate charging of output capacitor(s) within output circuit 22. As noted in the Nelson et al. '588 patent, it is generally necessary to include within output circuit 22 a DC-to-DC converter to convert electrical energy from the power supply for device 10—typically a low-voltage, low-current battery—to charge the output capacitor. A typical form of DC-to-DC converter is commonly referred to as a "flyback" converter, which employs a transformer having a primary winding in series with the power supply (battery) and a secondary winding in series with the output capacitor. An interrupting circuit or switch is placed in series with the primary coil and battery. Charging of the output capacitor is accomplished by inducing voltage in the primary winding of the transformer, creating a magnetic field in the secondary winding. When the current in the primary winding is interrupted, the collapsing field develops a current in the secondary winding which is applied to the output capacitor to charge it. The repeated interruption of the supply current charges the output capacitor to a desired level over time. Thereafter, the output capacitor is incrementally discharged to the patient's heart as described in detail above, resulting in the delivery of the multi-phase fibrillation-inducing pulse as described above with reference to FIGS. 1 and 2.

Figure 3:
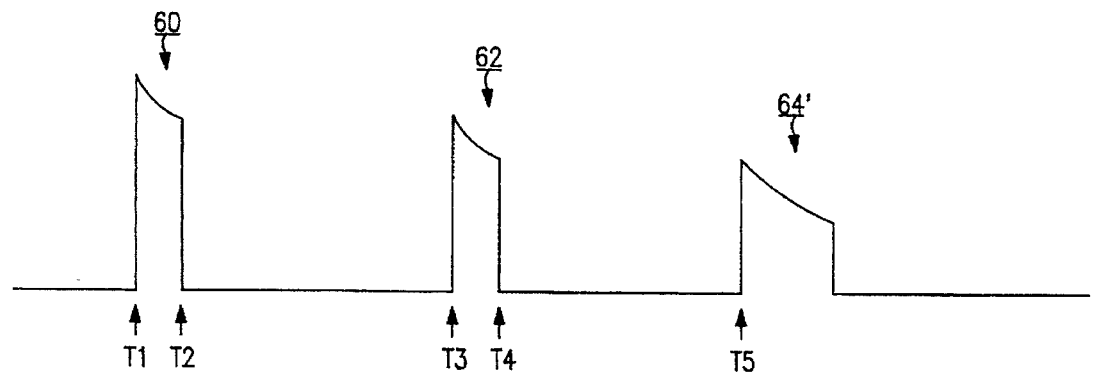
FIG. 3 illustrates an alternative embodiment of the multi-phase fibrillation-inducing waveform in accordance with the present invention.

An alternative embodiment of the multi-phase fibrillation-inducing waveform in accordance with the present invention is depicted in FIG. 3. The waveform of FIG. 3 differs from that of FIG. 2 in that the last phase 64' is truncated.

Figure 4:
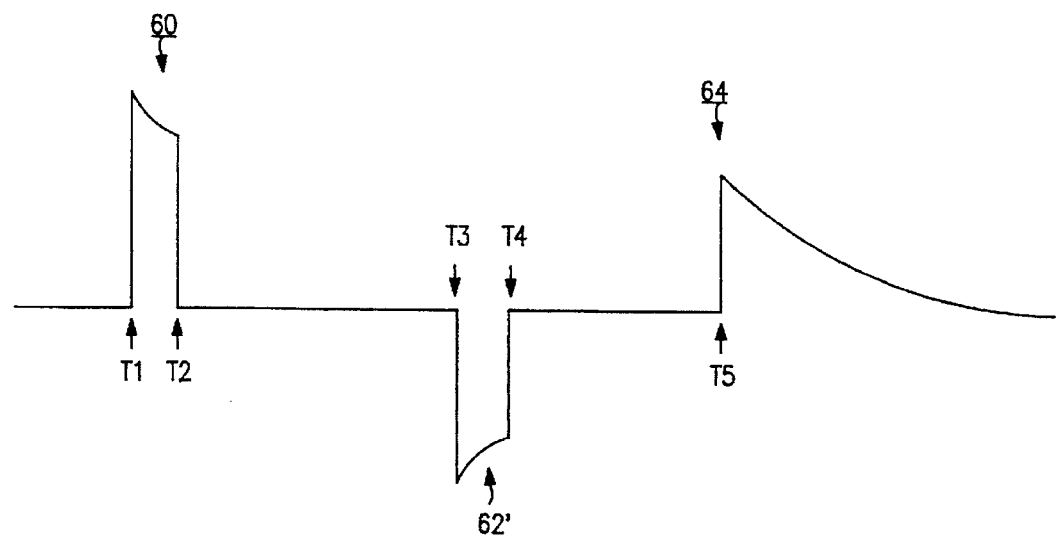
FIG. 4 illustrates another alternative embodiment of the multi-phase fibrillation-inducing waveform in accordance with the present invention.

Another alternative embodiment of the invention is depicted in FIG. 4, which shows a multi-phase fibrillation-inducing waveform in which the second phase 62' is of opposite polarity from the first phase 60.

Although reference has been made herein to the Nelson et al. '588 patent in connection with a specific implementation of output circuit 22 suitable for the purposes of practicing the present invention, it is believed that numerous other known circuits for generating the necessary energy for delivery of the multi-phase pulse would also be suitable.

In conjunction with the above disclosure, we claim:

1. A method of inducing fibrillation in a patient's heart, comprising the steps of:

(a) charging an energy storage device to a predetermined level;

(b) determining said patient is not fibrillating and while said patient is not fibrillating, discharging said energy storage device to said heart in a plurality of successive increments to produce a plurality of pulses of decreasing amplitude separated by an interval substantially greater than widths of said pulses and applying said pulses to said patient's heart.

2. A method in accordance with claim 1, comprising determining a time interval less than said patient's vulnerability window and wherein said discharging step comprises producing first and second ones of said plurality of pulses separated by said determined time interval.

3. An apparatus for inducing fibrillation in a patient's heart, comprising:

means for defining a coupling interval following a depolarization of a chamber of a patient's heart;

an output circuit having an energy storage device therein, and means for discharging energy stored on said energy storage device, said output circuit adapted to be coupled to a patient's heart via at least one conductive lead;

a control circuit, coupled to said defining means and said output circuit and adapted to successively trigger said discharging means on expiration of said coupling interval to incrementally discharge said energy storage means to deliver a series of pulses of decreasing magnitude at inter-pulse intervals substantially greater than the widths of the pulses but less than the duration of a predetermined vulnerability window of a typical patient's heart.

4. An apparatus in accordance with claim 3, wherein said inter-pulse intervals are less than 300 ms.

5. An apparatus in accordance with claim 3, wherein said inter-pulse intervals are 50–300 ms.

6. An apparatus in accordance with claim 3, wherein said series of pulses includes pulse having a 2 ms pulse width.

7. An apparatus in accordance with claim 3, wherein said series of pulses includes inter-pulse intervals 25–150 times greater than pulse widths of said pulses.

8. An apparatus in accordance with any of claims 3–7 wherein the last of said series of pulses comprises an untruncated discharge of remaining energy stored on said energy storage device.

9. An apparatus in accordance with any of claims 3–7 wherein said discharging means comprises means for discharging said energy storage device to successively generate pulses of opposite polarity.

10. A method of inducing fibrillation in a patient's heart, comprising:

applying electrodes to said patient;

determining inter pulse intervals;

defining a coupling interval following a depolarization of a chamber of a patient's heart;

charging an energy storage device coupled to said electrodes; and on expiration of said coupling interval, and while said patient is not fibrillating, successively discharging said storage means through said electrodes to incrementally discharge said energy storage means to deliver a series of pulses of decreasing magnitude separated by said interpulse intervals.

11. A method according to claim 10 wherein said determining step comprises determining interpulse intervals substantially greater than the widths of said pulses.

12. A method according to claim 10 wherein said determining step comprises determining interpulse intervals less than the duration of the vulnerability window of a said patient's heart.

13. A method according to claim 10 wherein said determining step comprises determining interpulse intervals less than the duration of the vulnerability window of a typical patient's heart.

14. A method according to claim 10 wherein said discharging step comprises delivering the last of said pulses as an untruncated discharge of remaining energy stored on said energy storage device.

15. An apparatus in accordance with any of claims 10–14 wherein said discharging step comprises discharging said energy storage device to successively generate pulses of opposite polarity.

* * * * *